United States Patent [19]

Sauer et al.

[11] Patent Number: 4,695,635
[45] Date of Patent: Sep. 22, 1987

[54] PROCESS FOR THE PRODUCTION OF 2,3-DIHYDROERGOLINES

[75] Inventors: Gerhard Sauer; Gregor Haffer, both of Berlin, Fed. Rep. of Germany

[73] Assignee: Schering Aktiengesellschaft, Berlin and Bergkamen, Fed. Rep. of Germany

[21] Appl. No.: 717,064

[22] Filed: Mar. 28, 1985

[30] Foreign Application Priority Data

Mar. 28, 1984 [DE] Fed. Rep. of Germany ....... 3411981

[51] Int. Cl.[4] .......................................... C07D 487/06
[52] U.S. Cl. ...................................... 546/69; 546/67; 546/68
[58] Field of Search ............................. 546/67, 68, 69

[56] References Cited

FOREIGN PATENT DOCUMENTS 1596210 8/1961 United Kingdom .

OTHER PUBLICATIONS

Gribble, et al., "Reactions of Sodium Borohydride in Acidic Media I.," *J.A.C.S.* 96, (1974) pp. 7812-7814.

Groves, et al., "Dehalogenations with Sodium Borohydride, ..." *J.A.C.S.* 96, (1974) pp. 6527-6529.

Okolobdzija, et al., New Synthesis of 2-(2',2',2'-Trifluoroethyl)-Amino-5-Chlorobenzophenone ...", *Chem. Abst.* 94: 121481(g) (1981).

Rolla, Franco, "Sodium Borohydride Reductions Under Phase Transfer Conditions, ...", *J. Org. Chem.* 46 (1981) pp. 3909-3911.

"Dimerization of Ergot Derivatives", Tetrahedron Let. pp. 3315-3316, 1973, N. J. Bach and E. C. Kornfeld.

*Primary Examiner*—Donald G. Daus
*Assistant Examiner*—C. Shen
*Attorney, Agent, or Firm*—Millen & White

[57] ABSTRACT

2-bromoergolines can be reduced in good yields, without dimerization as determined by NMR product analysis, to the corresponding 2,3-dihydroergolines under otherwise conventional reducing conditions by introducing 2-bromoergolines, together with sodium borohydride, into trifluoroacetic acid under cooling to prevent the reaction mixture from rising above ambient temperature.

17 Claims, No Drawings

PROCESS FOR THE PRODUCTION OF 2,3-DIHYDROERGOLINES

BACKGROUND OF THE INVENTION

This invention relates to a method for the preparation of 2,3-dihydroergolines.

The 2,3-dihydroergolines that can be prepared according to this invention and biologically active compounds, or intermediates useful in the production of biologically efficacious compounds, which exhibit an effect on the central nervous system, see for reference, e.g., U.S. Ser. No. 589,376.

The preparation of 2,3-dihydroergolines per se is conventional and has been described in GB No. 1,596,210. According to this process, the ergoline derivative is reduced with sodium borohydride in trifluoroacetic acid. Although giving good yields for a number of ergoline derivatives, this process disadvantageously leads to dimerization products, e.g. in the cases of lisuride or terguride (cf. N. K. Bach and E. C. Kornfeld, Tetrahedron Letters 3315 (1973). Formation of these dimerization products becomes more pronounced with larger charges of starting material.

SUMMARY OF THE INVENTION

Accordingly, it is a general object of the present invention to provide a process for the preparation of 2,3-dihydroergolines which minimize the drawbacks of the aforementioned prior art process.

Another object of the present invention is to provide a process for the preparation of 2,3-dihydroergolines in high yields.

A further object of the present invention is to provide a process for the preparation of 2,3-dihydroergolines which essentially eliminates the formation of undersired dimerization by-products.

An additional object of the present invention is to permit formation of isomers in ratios determined solely by the structure of the 2-bromoergoline starting material.

Upon study of the specification and appended claims, further objects, features and advantages of the present invention will become more fully apparent to those skilled in the art to which this invention pertains.

It has now surprisingly been found that 2-bromoergolines can be reduced in good yields, without dimerization (e.g., as determined by NMR product analysis), to the corresponding 2,3-dihydroergolines under otherwise conventional reducing conditions by introducing 2-bromergoline, together with sodium borohydride, into trifluoroacetic acid under cooling to prevent the reaction mixture from rising above ambient temperature, e.g. 25°–30° C.

DETAILED DISCUSSION

The process is performed with exclusion of air on account of hydrogen evolution, and the sodium borohydride is preferably utilized in stoichiometric excess, e.g., 5–10 times the stoichiometric amount.

It proved to be practical to prevent the reaction temperature from rising above ambient room temperature. On the other hand, low temperatures (down to −20° C.) merely have the effect of prolonging the reaction time. Under ambient temperature, reaction times usually are 2–10 hours.

The reaction temperature has no influence on the ratio of isomers. It has been found that, depending on the specific structure of the 2-bromoergoline, a wide variety of mixtures of 3βH- and αH-isomers can be formed; the ratio can essentially be anywhere between 100:0 and 50:50, as determined by NMR.

Unless otherwise described herein, reaction conditions are as disclosed in GB No. 1,596,210.

The 2,3-dihydroergoline products produced in accordance with the present invention are generally those having the general formula:

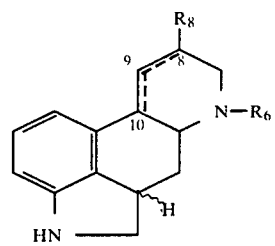

wherein $C_8 = C_9$ and $C_9 = C_{10}$ are each a C—C single or C=C double bond, but are not both a C=C double bond, $R_6$ is lower alkyl of up to 3 carbon atoms, and $R_8$ is —CH$_3$, —NH—CO—N(C$_2$H$_5$)$_2$ or —COOCH$_3$.

Typical starting materials include:

3-(2-bromo-9,10-didehydro-6-methyl-8-αergolinyl)-1,1-diethylurea;

3-(2-bromo-6-methyl-8α-ergolinyl)-1,1-diethylurea;

3-(2-bromo-6-n-propyl-8α-ergolinyl)-1,1-diethylurea;

2-bromo-9,10-didehydro-6-methylergoline-8β-carboxylic acid methyl ester;

3-bromo-6-methyl-8β-ergolinecarboxylic acid methyl ester; and 3-bromo-8,9-didehydro-6,8-dimethylergoline.

The starting materials are all known or readily preparable from known starting materials, see for reference, e.g. U.S. Ser. No. 339,566.

The sodium borohydride and the starting bromoergoline can be added separately to the trifluoracetic acid, preferably the bromoergoline is added first. They also can be added to the acid together.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight.

EXAMPLE 1

In an ice bath, 280 ml of trifluoroacetic acid is cooled and then successively combined, under inert gas, with 12.5 g of 3-(2-bromo-9,10-didehydro-6-methyl-8α-ergolinyl)-1,1-diethylurea (30 millimoles) and 7 g of sodium borohydride in tablet form. The mixture is stirred under ice cooling for 4 hours and, during this time, 2×3 g of sodium borohydride is added. Then the reaction mixture is poured on about 200 ml. of ice and, under ice cooling, gently neutralized with concentrated aqueous ammonia solution (32%). The mixture is extracted with methylene chloride, and the organic phase is then dried with magnesium sulfate and evaporated.

The residue is crystallized from ethyl acetate and diisopropyl ether, thus obtaining 6.35 g of 3-(9,10-didehydro-2,3β-dihydro-6-methyl-8α-ergolinyl)-1,1-diethylurea (62% of theoretical). From the mother liquor, another 1.0 g of compound is additionally crystallized. According to NMR analysis, the compound is solely a 3βH-compound.

$[\alpha]_D = +207°$ (0.5% in chloroform).

EXAMPLE 2

Following the general procedure of Example 1 but substituting 3-(2-bromo-6-methyl-8α-ergolinyl)-1,1-diethylurea as a starting material, 3-(2,3-dihydro-6-methyl-8-ergolinyl)-1,1-diethylurea was obtained with a crude yield of 85%. According to NMR, this is a mixture of 60% of the 3βH- and 40% of the 3αH-compounds.

The pure 3βH-compound has a rotation value $[\alpha]_D = +44°$ (0.5% in chloroform).

EXAMPLE 3

Following the general procedure of Example 1 but substituting 3-(2-bromo-6-n-propyl-8α-ergolinyl)-1,1-diethylurea as the starting material, 3-(2,3-dihydro-6-n-propyl-8α-ergolinyl)-1,1-diethylurea is obtained with a crude yield of 88%. According to NMR, this is a mixture of 50% 3αH-compound and 50% 3βH-compound.

The pure 3βH-compound has the rotation value $[\alpha]_D = +14°$ (0.5% in chloroform).

EXAMPLE 4

Following the general procedure of Example 1 but substituting 2-bromo-9,10-didehydro-6-methylergoline-8β-carboxylic acid methyl ester as the starting material, 9,10-didehydro-2,3-dihydro-6-methylergoline-8-carboxylic acid methyl ester was obtained with a crude yield of 74%. According to NMR, the reaction product constitutes a 1:1 mixture of the 3αH- and the 3βH-compounds.

The rotation values are without significance for this compound, since the asymmetric center in the 8-position is also isomerized in trifluoroacetic acid.

EXAMPLE 5

Following the general procedure of Example 1 but substituting 3-bromo-6-methyl-8β-ergolinecarboxylic acid methyl ester as the starting material, 2,3-dihydro-6-methyl-8β-ergolinecarboxylic acid methyl ester was formed with a crude yield of 86%. According to NMR, the reaction product represents a mixture of 60% of the 3αH- and 40% of the 3βH-compounds.

$[\alpha]_D = -16°$ (0.5% in chloroform).

EXAMPLE 6

Following the general procedure for Example 1 but substituting 3-bromo-8,9-didehydro-6,8-dimethylergoline as the starting material, 2,3-dihydro-8,9-didehydro-6,8-dimethylergoline was formed with a crude yield of 85%. According to NMR, the reaction product constitutes a mixture of 85% of the 3βH- and 15% of the 3αH-compounds.

$[\alpha]_D = -0.5°$ (0.5% in chloroform).

The preceding examples can be repeated with similar success by substituting the generically or specifically described reactants and/or operating conditions of this invention for those specifically used in the examples. From the foregoing description, one skilled in the art to which this invention pertains can easily ascertain the essential characteristics thereof and, without departing from the spirit and scope of the present invention, can make various changes and modifications to adapt it to various usages and conditions.

What is claimed is:

1. In a process for the production of a 2,3-dihydroergoline of the general formula

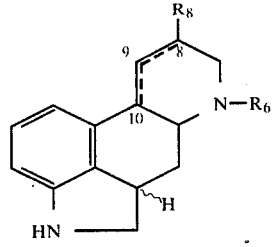

wherein
$C_8 === C_9$ and $C_9 === C_{10}$ are each a C—C single or C=C double bond, but are not both a C=C double bond, $R_6$ is a lower alkyl group of up to 3 carbon atoms, and
$R_8$ is —CH$_3$, —NH—CO—N(C$_2$H$_5$)$_2$ or —COOCH$_3$, by reducing the corresponding 2-bromoergoline with sodium borohydride in trifluoroacetic acid, the improvement which comprises:

conducting the reduction step under cooling, whereby dimerization side reactions are essentially eliminated or lessened.

2. A process according to claim 1 wherein a stoichiometric excess of sodium borohydride is employed and the reaction is carried out in an inert gas atmosphere.

3. A process according to claim 1 wherein the 2-bromoergoline starting material is selected from the group consisting of:

3-(2-bromo-9,10-didehydro-6-methyl-8-αergolinyl)-1,1-diethylurea;

3-(2-bromo-6-methyl-8α-ergolinyl)-1,1-diethylurea;

3-(2-bromo-6-n-propyl-8α-ergolinyl)-1,1-diethylurea;

2-bromo-9,10-didehydro-6-methylergoline-8β-carboxylic acid methyl ester;

3-bromo-6-methyl-8β-ergolinecarboxylic acid methyl ester; and 3-bromo-8,9-didehydro-6,8-dimethylergoline.

4. A process according to claim 3 wherein cooling is sufficient to prevent the reaction temperature from rising above ambient temperature, a stoichiometric excess of sodium borohydride is employed, and the reaction is carried out in an inert gas atmosphere.

5. In a process for the production of a 2,3-dihydroergoline of the general formula

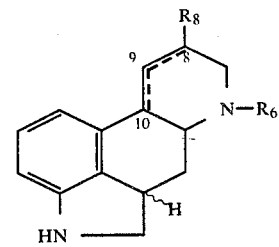

wherein
$C_8 === C_9$ and $C_9 === C_{10}$ are each a C—C single or C=C double bond, but are not both a C=C double bond, $R_6$ is a lower alkyl group of up to 3 carbon atoms, and $R_8$ is —$CH_3$, —NH—CO—N($C_2H_5$)$_2$ or —COOCH$_3$, by reducing the corresponding 2-bromoergoline with sodium borohydride in trifluoroacetic acid, the improvement which comprises:

introducing the 2-bromoergoline and sodium borohydride into the trifluoroacetic acid with sufficient cooling to maintain the reaction temperature at ambient temperature or lower.

6. A process of claim 1, wherein $C_8$ — $C_9$ is a double bond.

7. A process of claim 1 wherein $C_9$ — $C_{10}$ is a double bond.

8. A process of claim 1 wherein both $C_8$ — $C_9$ and $C_9$ — $C_{10}$ are single bonds.

9. A process of claim 1 wherein $R_6$ is methyl.

10. A process of claim 1 wherein $R_8$ is $CH_3$.

11. A process of claim 1 wherein $R_8$ is —NH—CO—N($C_2H_5$)$_2$.

12. A process of claim 1 wherein $R_8$ is —COOCH$_3$.

13. A process of claim 1 wherein said cooling is sufficient to maintain the reaction temperature below about 30° C.

14. A process of claim 1 wherein the reaction is conducted substantially in the absence of air.

15. A process of claim 1 wherein the reaction time is from 2–10 hours.

16. A process of claim 1 wherein said cooling is sufficient to maintain a reaction temperature of from about 20° to about 30° C.

17. A process of claim 1 wherein the introduction of 2-bromoergoline and sodium borohydride is conducted under cooling.

* * * * *